United States Patent [19]

Sheen et al.

[11] Patent Number: 5,557,283

[45] Date of Patent: *Sep. 17, 1996

[54] REAL-TIME WIDEBAND HOLOGRAPHIC SURVEILLANCE SYSTEM

[76] Inventors: David M. Sheen, 1917 Hood; H. Dale Collins, 1751 Duluth, both of Richland, Wash. 99352; Thomas E. Hall, 8301 W. Entiat Pl., Kennewick, Wash. 99336; Douglas L. McMakin, 2173 Shasta Ave., Richland, Wash. 99352; R. Parks Gribble, 1215 Cottonwood Dr., Richland; Ronald H. Severtsen, 1803 Birch Ave., Richland, Wash. 99352; James M. Prince, 3029 W. 2nd Ave., Apt. F95, Kennewick, Wash. 99336; Larry D. Reid, Rt. 1, Box 1291B, Benton City, Wash. 99320

[ * ] Notice: The term of this patent shall not extend beyond the expiration date of Pat. No. 5,455,590.

[21] Appl. No.: 440,279

[22] Filed: May 12, 1995

Related U.S. Application Data

[63] Continuation-in-part of Ser. No. 212,432, Mar. 14, 1994, Pat. No. 5,455,590, which is a continuation-in-part of Ser. No. 963,204, Nov. 23, 1992, abandoned, which is a continuation-in-part of Ser. No. 752,750, Aug. 30, 1991, abandoned.

[51] Int. Cl.$^6$ ............................. G01S 13/89; G03H 5/00
[52] U.S. Cl. .................................. 342/179; 367/8
[58] Field of Search ................................. 342/179; 367/8

[56] References Cited

U.S. PATENT DOCUMENTS 5,073,782  12/1991  Huguenin et al. ...................... 342/179
5,170,170  12/1992  Soumekh ................................. 342/179
5,455,590  10/1995  Collins et al. .......................... 342/179

OTHER PUBLICATIONS

Osumi et al, "Detection of Buried Objects", 1EE Proceedings, vol. 135, No. 4, Aug. 1988.
Boyer A. L., "Reconstruction of Ultrasonic Images By Backward Propagation", CH. 18, Jul. 1970, pp. 333–349.
K. Sigfrid Yngvesson, Daniel H. Schaubert, Thomas L. Korzeniowski, Erik L. Kollberg, Thomas Thungren, and Joakim F. Johansson; "Endfire Tapered Slot Antennas on Dielectric Substrates"; *IEEE Transactions on Antennas and Propagation*, vol. SP-33, No. 12, pp. 1392–1400; Dec. 1985.
G. Tricoles and Nabil H. Farhat; "Microwave Holography: Applications and Techniques": *Proceedings of the IEEE*, vol. 65, No. 1, pp. 108–121; Jan. 1977.
NH Farhat; "High Resolution Microwave Holography and the Imaging of Remote Moving Objects"; *Optical Engineering*, Sep.–Oct. 1975, vol. 14, No. 5; pp. 499–505; 1975.
G. F. Abbott; "Personal Surveillance System"; *IBM Technical Disclosure Bulletin*, vol. 12, No. 7; pp. 1119–1120; Dec. 1969.

*Primary Examiner*—Ian J. Lobo

[57] ABSTRACT

A wideband holographic surveillance system including a transceiver for generating a plurality of electromagnetic waves; antenna for transmitting the electromagnetic waves toward a target at a plurality of predetermined positions in space; the transceiver also receiving and converting electromagnetic waves reflected from the target to electrical signals at a plurality of predetermined positions in space; a computer for processing the electrical signals to obtain signals corresponding to a holographic reconstruction of the target; and a display for displaying the processed information to determine nature of the target. The computer has instructions to apply a three dimensional backward wave algorithm.

24 Claims, 13 Drawing Sheets

$T_0$ to $T_1$ = 1.5 μsec

REAL-TIME WIDEBAND HOLOGRAPHIC SURVEILLANCE SYSTEM

STATEMENT OF GOVERNMENT INTEREST

This invention was made with Government support under Contract DE-AC06-76RLO 1830, awarded by the U.S. Department of Energy. The Government has certain rights in the invention.

This application is a Continuation-In-Part of U.S. patent application Ser. No. 08/212,432, filed Mar. 14, 1994, now U.S. Pat. No. 5,455,590, which is a Continuation-In-Part of U.S. patent application Ser. No. 07/963,204, filed Nov. 23, 1992, now abandoned, which is a Continuation-In-Part of U.S. patent application. Ser. No. 07/752,750, filed Aug. 30, 1991, now abandoned.

FIELD OF THE INVENTION

The present invention relates to a method and apparatus useful for inspection of concealed objects. More specifically, the present invention relates to use of backward wave propagation analysis with millimeter wave signals that are transmitted and received by a holographic array. The method and apparatus have particular utility for personnel inspection in mass transportation centers. Still more specifically, the present invention relates to use of wideband millimeter wave signals with a three dimensional backward wave propagation analysis.

BACKGROUND AND RELATED ART

The need for a new and more versatile personnel inspection system in mass transportation centers has increased in recent years. Traditional inspection systems such as metal detectors and X-ray imaging systems, although capable of near real-time detection, have limitations and adverse effects in the detection of concealed targets. Limitations of metal detectors include the inabilities to (a) provide precise target location, (b) detect plastic concealed weapons, and (c) detect certain metals because of sensitivity variation for various metals. Limitations of X-ray imaging of personnel include radiological health effects. Consequently, millimeter wave holography has been under investigation as an alternative or complementary approach to personnel inspection.

Related holographic art known to the inventors includes the following. A report, EVALUATION OF PASSIVE FAR INFRARED RADIOMETRIC TECHNIQUES FOR DETECTION OF CONCEALED OBJECTS, DT Hodges et al., Aerospace Report No. ATR-79(7745)-1, Contract No. At-(29-1)789, Sandia Laboratories, Albuquerque, N.Mex., 87115, March 1979, p. 41, discloses apparatus and a process for far infrared detection of concealed objects. U.S. Pat. No. 4,841,489 to Ozaki et al. discloses a method for imaging an object or substance by ultrasonic or electromagnetic waves based on a synthetic aperture method capable of economizing memory capacity, achieving real-time base image reproduction, and obtaining a high quality image.

Application of holography to the problem of personnel surveillance has been limited because of the inability to either (a) produce an image of sufficient resolution, or (b) produce an image in near real-time, or (c) a combination of both. It is recognized that use of millimeter wave electromagnetic radiation is not a physiological health hazard and such radiation penetrates certain materials, including but not limited to clothing.

Prior work as reported by NH Farhat, HIGH RESOLUTION MICROWAVE HOLOGRAPHY AND THE IMAGING OF REMOTE MOVING OBJECTS, Optical Engineering, Sep.–Oct. 1975, Vol. 15, No. 5, pp. 499–505, utilized millimeter wave holography in working toward surveillance systems. However, Farhat did not obtain high resolution because he used f-numbers greater than 1.0. Moreover, he could not achieve near real-time imaging because he used an optical reconstruction technique.

Hildebrand and Brenden, AN INTRODUCTION TO ACOUSTICAL HOLOGRAPHY, 1972, Plenum Press, New York, N.Y, demonstrated excellent resolution with acoustical holography using optical reconstruction and a low f-number. However, it is recognized that acoustical holography is impractical for personnel surveillance because of the coupling fluid required between the acoustic transmit/receive element and the target. Moreover, Hildebrand and Brenden used optical reconstruction that cannot achieve near real-time imaging.

Both Farhat and Hildebrand et al. used optical reconstruction to produce images with their holograms. Another reconstruction technique is digital reconstruction wherein the signal reflected from the target in the form of acoustic or electromagnetic radiation is converted into a digital electronic signal that is mathematically converted into information that is useful for producing an image of the target. Even using digital reconstruction techniques, however, high resolution is not always obtainable because the reconstruction techniques inherently limit image resolution.

There are standard digital reconstruction techniques that have been used for processing millimeter wave data. For example, a widely used method is to apply a fast Fourier transform to the Kirchoff diffraction integral. However, this method uses a finite sum written in the small angle (Fresnel) approximation that limits the relationship between aperture size and distance to the target, inherently limiting the f-number to be at least 6, and thereby limiting resolution of holographic image reconstruction.

A digital reconstruction method that overcomes this limitation is reported by AL Boyer et al., RECONSTRUCTION OF ULTRASONIC IMAGES BY BACKWARD PROPAGATION, Reconstruction of Holographic Images, Chapter 18, July 1970. The so-called angular spectrum backward wave propagation method does not use the Fresnel approximation and can therefore be used for low f-number reconstruction. However, the angular spectrum method has not been widely used for holographic imaging because it is generally believed that the recording plane must be very stable and flat within a small fraction of the wavelength. A thesis by HD Collins, June 1970, demonstrates that the recording plane need not be flat within a wavelength. Another reason that the angular spectrum method has not been widely used is that it is computationally intensive.

A two-dimensional image reconstruction algorithm is implemented in U.S. Pat. No. 5,170,170 issued Dec. 8, 1992, to Soumekh. Soumekh derived a wideband SAR (synthetic aperture radar) imaging algorithm which reconstructs data from a linear aperture into a two-dimensional image. This technique, as with all SAR techniques, is not well suited to personnel surveillance imaging because it is limited to use with a linear aperture, rather than a two-dimensional aperture.

The second fundamental limitation preventing wide use of millimeter wave holography for personnel surveillance is the amount of time required to scan a target. Boyer et al. acoustic target scanning required 50 minutes to obtain 300 samples/second in 256 scan lines. Boyer et al. restricted scan rates to obtain highest spatial frequency. Use of a single antenna element moved from position to position for 65,000 positions across an aperture has been accomplished in 5 minutes. To be useful in surveillance, it is necessary to perform a scan within several seconds and preferably in one second or less.

In holography, fast scans with high resolution are difficult to achieve. Resolution is highest when the millimeter wave signal is transmitted and received from the same antenna element. As previously indicated, moving a single element to hundreds of positions is physically limited to scan times on the order of minutes. Use of separate transmit and receive arrays severely limits the resolution of the reconstructed image. Examples of scanning systems include various arrangements of antenna types and arrays.

Antenna arrays have been used as reported in Tricoles et al., MICROWAVE HOLOGRAPHY: APPLICATIONS AND TECHNIQUES, Proceedings of the IEEE, Vol. 65, No. 1, Jan. 1977. In FIGS. 4 and 5 of Tricoles et al., arrays are shown wherein antenna element spacing is much greater than a wavelength of the microwaves and there are separate transmit and receive arrays.

Larson et al., MICROWAVE HOLOGRAM RADAR IMAGERY, February 1972, show a far-field microwave holographic imaging system having a single transmit horn antenna and a separate receiver array of 100 elements spaced slightly more than ½ wavelength apart. FIG. 11 of Larson et al. shows an image of a Jeep made with this system. The image resolution is coarse, 15 cm (½ foot) by 15 cm (½ foot).

The current state-of-the-art in millimeter-wave imaging systems may be summarized by two fundamentally different techniques. The first technique uses a focal-plane two-dimensional array of millimeter-wave detectors placed behind a large lens as described in U.S. Pat. No. 5,073,782 issued Dec. 17, 1991, to Huguenin et al. Huguenin et al. detect either passive energy emitted by the target or active energy emitted by millimeter-wave illuminators. Advantages of Huguenin et al. include: possible real-time operation, relatively compactness, and operation analogous to an optical camera. Disadvantages include: relatively low resolution due to the high optical f-number of a practical configuration, small aperture (lens size is limited by practical constraints), and limited field of view.

The second technique uses a holographic linear array of sequentially-switched transmitter-receivers scanned quickly over a large aperture to actively illuminate the target as described in U.S. Pat. No. 5,455,590 issued Mar. 14, 1994 to Collins et al. Collins et al. use a single frequency that is coherent, which means the phase of the returned signal is recorded as well as the amplitude. The coherent data is reconstructed in a computer to form a focused image of a target without the need for a lens. Advantages of this technique include: near real-time operation, very high-resolution (due to low optical f-number), computer reconstruction allows focusing at any depth, and large aperture (full body field of view). The primary disadvantage of this system/technique is that the close-range, large aperture operation causes the depth of focus to be very short. Therefore, the image of a target with significant depth, such as the human body cannot be reconstructed in complete focus. A further limitation of Collins et al. is interference from a cover that is placed between the person to be imaged and the transceiver system. The cover vibrates thereby producing an interference in the signals between the person and the transceiver system. While it is possible to subtract out some of the interference, it is not possible to remove it completely because the cover does not always vibrate in the same manner. Hence, resolution is limited to the extent of remaining cover interference.

Thus, there is a need for a holographic image reconstruction method and apparatus that can provide high resolution with fast scanning and fast reconstruction algorithm and that has an expanded depth of field to accomplish near real-time imaging that is needed for personnel surveillance.

BRIEF DESCRIPTION OF THE INVENTION

The present invention is an extension of the holographic imaging system from single-frequency operation to wideband (many or a plurality of frequencies) operation. Rather than forming two-dimensional images reconstructed at a variety of frequencies, wideband imaging permits forming a fully-focused, three-dimensional image. The data are gathered over a two-dimensional aperture. The use of wideband imaging completely overcomes the limitation present in a single frequency or multiple single frequency system. In this specification, the term wideband refers to integrated sending and receiving of at least two frequencies, as opposed to separate sending and receiving of at least two frequencies.

To achieve wide-band imaging, a number of components and techniques were replaced in the single frequency system. The single frequency transceiver in the system described in Collins et al. had to be replaced with a transceiver capable of sweeping a wide frequency bandwidth. A novel image reconstruction computer algorithm was developed to allow efficient volumetric (3-D) image reconstruction. The switch/antenna array was modified to operate over a wide-bandwidth.

The present invention disclosed herein involves a method and apparatus for achieving near real-time holographic imaging of concealed objects. Millimeter wave radiation having frequencies from about 1 GHz to about 100 GHz is used. While a minimum of 2 frequencies is possible, it is preferred to use at least 16 frequencies for efficient algorithm analysis, and most preferred to use at least 64 frequencies for good image quality and accurate data sampling. However, any number of frequencies may be used consistent with the expression $N_f = (4BR)/c$ where $N_f$ = number of frequencies B = bandwidth R = range extent or depth, and c = speed of light.

Bandwidth may range from about 1% to about 200%, but is a trade-off between performance and cost. High bandwidths offer the advantage of high range resolution but are more difficult to process because of hardware limitations. Accordingly, bandwidths on the order of from about 10% to about 50% are preferred.

The range extent, or target distance from antenna, may theoretically range from about 1 cm to about 10 m. In a real system, however, the range extent is practically limited to from about 10 cm to about 1.5 m. Signal strength affected by range and source strength is a factor that affects resolution.

High resolution is preserved in the image reconstruction by using a three-dimensional image reconstruction algorithm according to the present invention. This three-dimensional algorithm avoids any approximation that would limit image resolution. Image resolution is therefore limited by the diffraction limit and by the spatial sampling. A person, or other target may be from about 10 cm to about 150 cm from the transceiver system.

The image reconstruction algorithm derived for the present invention is an extension of Soumekh by making the aperture planar instead of linear which permits a fully three-dimensional image reconstruction. Notation used herein is consistent with that used by Soumekh. The reconstruction algorithm can also be considered to be an extension of the single frequency "backward wave" holographic reconstruction algorithm in Boyer to wideband.

DETAILED DESCRIPTION OF THE INVENTION

The following description begins with a derivation of a wideband reconstruction algorithm followed by a description of a wideband holographic imaging system. Operational Examples are then provided.

DERIVATION

Figure 1A:
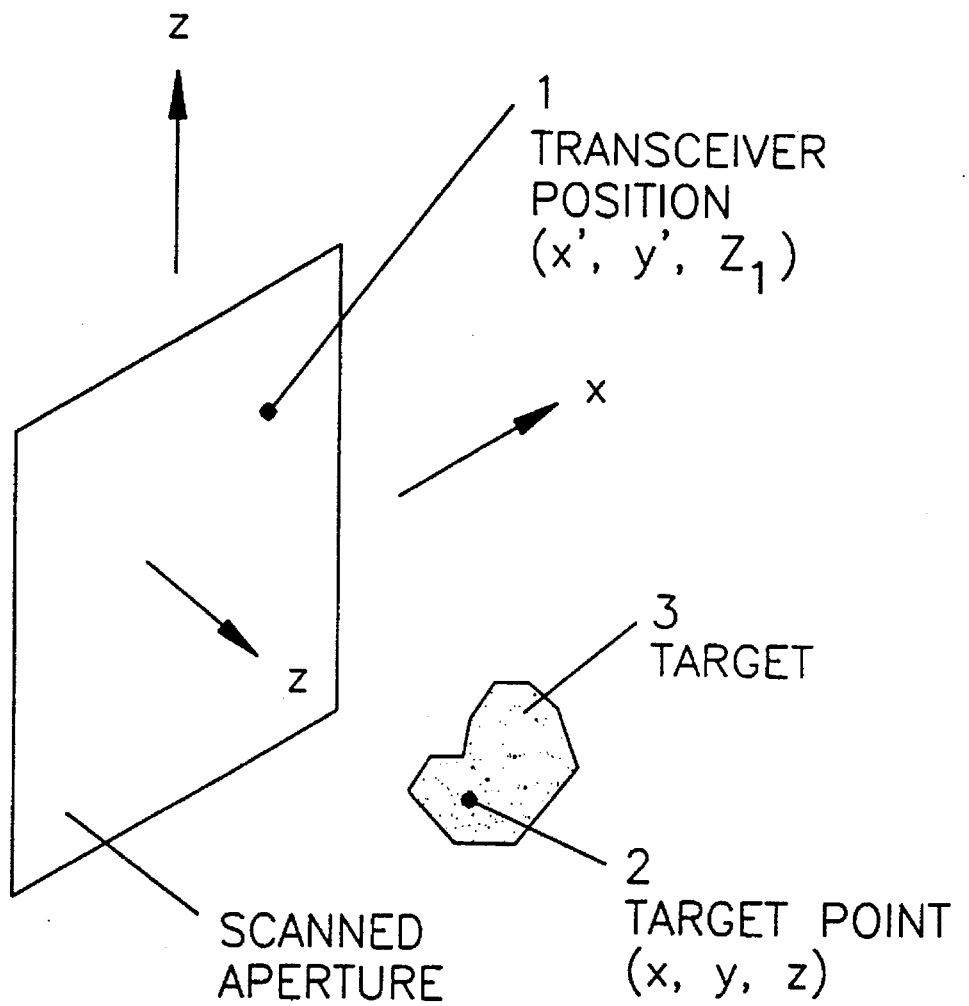
FIG. 1a is a coordinate definition diagram.

The measurement configuration is shown in FIG. 1a, where the primed coordinates represent the transceiver position (1), and the unprimed coordinates represent a single target point (2) in the target or image space (3). If the target (3) is characterized by a reflectivity function, $f(x,y,z)$, then the response measured at the transceiver position (1) will be the superposition of the reflectivity function times the round trip phase to the target (3). The measurement plane (not shown) is at $z=Z_1$, which is typically negative. The round-trip phase is $$2k\sqrt{(x-x')^2+(y-y')^2+(z-Z_1)^2} \quad (1)$$

The response measured at the transceiver position (1) is $$s(x',y',\omega) = \iiint f(x,y,z) e^{-j2k\sqrt{(x-x')^2+(y-y')^2+(z-Z_1)^2}} dxdydz \quad (2)$$

where $k=\omega/c$ is the wavenumber, and the amplitude decay with range is not considered since it will have little impact on focusing the image. If needed, amplitude decay with range may be compensated for in the raw data by applying a numerical gain to the data from the transceiver. The numerical gain increases with range.

Alternatively, the data could be collected in the time domain, as is common with acoustic data. In this case, the data in Equation 2 will be obtained by Fourier Transforming the gathered data $s_t(x',y',t)$, which is the echoed data in the time domain, $$s(x',y',\omega) = FT_{(t)}[s_t(x',y',t)] \quad (3)$$

The exponential term in Equation 2 represents a spherical wave which is decomposed into an infinite superposition of plane waves, $$e^{-j2k\sqrt{(x-x')^2+(y-y')^2+(z-Z_1)^2}} = \iint e^{-jk_x(x-x')-jk_y(y-y')-jk_z(z-Z_1)} dk_x dk_y \quad (4)$$

where $k_x$, and $k_y$, range from $-2k$ to $2k$ for propagating waves.

Using this decomposition into plane waves and rearranging yields $$s(x',y',\omega) = \iint \underbrace{[\iiint f(x,y,z) e^{-j(k_x x+k_y y+k_z z)} dxdydz]}_{F(k_x,k_y,k_z)} e^{jk_z Z_1} e^{jk_x x'} e^{jk_y y'} dk_x dk_y \quad (5)$$

where the triple integral between the brackets [] represents a three-dimensional Fourier Transform of the reflectivity function. Using this Fourier Transform relation, $$s(x',y',\omega) = \iint F(k_x,k_y,k_z) e^{jk_z Z_1} e^{j(k_x x'+k_y y')} dk_x dk_y \quad (6)$$
$$= FT_{2D}^{-1}\{F(k_x,k_y,k_z) e^{jk_z Z_1}\}$$

where FT is used to indicate Fourier Transformation.

Taking the 2-D Fourier Transform of both sides and dropping the distinction between the primed and unprimed coordinate systems yields $$FT_{2D}\{s(x,y,\omega)\} \equiv S(k_x,k_y,\omega) = F(k_x,k_y,k_z) e^{jk_z Z_1} \quad (7)$$

To utilize this relationship in the reconstruction of the target image, the frequency, $\omega$, needs to be expressed as a function of $k_z$. This is done by using the dispersion relation for plane waves in free-space or a uniform dielectric, $$k_x^2 + k_y^2 + k_z^2 = (2k)^2 = 4\left(\frac{\omega}{c}\right)^2 \quad (8)$$

Using this relation and inverting Equation 7 yields, $$f(x,y,z) = FT_{3D}^{-1}\{F(k_x,k_y,k_z)\} \quad (9)$$

where $$F(k_x,k_y,k_z) = S(k_x,k_y,\omega) e^{-jk_z Z_1} \quad (10)$$

Equation 10 suffices for the reconstruction of the image if the data is defined continuously in x, y, and ω; however, for practical imaging configurations, the data will be discretely sampled at uniform intervals of position and frequency. Therefore the data s(x,y,ω) is assumed to be uniformly sampled in each variable. Since the data is uniformly sampled in x and y, the 2-D Fast Fourier Transform may be used to obtain a sampled version of $S(k_x, k_y, \omega)$. Since the angular frequency, ω, is a function of $k_x$, $k_y$, and $k_z$, this data will contain samples of $F(k_x, k_y, k_z)$. However, these samples are non-uniformly spaced in $k_z$. The samples will be uniformly spaced in $k_x$ and $k_y$, and will lie on concentric spheres of radius 2k. In order to perform the inverse 3-D FFT in Equation 9, the data will need to be resampled to uniformly spaced positions in $k_z$. This is easily accomplished using linear interpolation techniques.

Image Reconstruction Algorithm

The steps required to implement the reconstruction technique on a computer are outlined below. The data is discretized in x,y,ω) and the image is discretized in (x,y,z). Fourier Transforms will typically be done using the discrete Fast Fourier Transform algorithm.

Reconstruction Algorithm

1. Gather sampled data, s(x,y,ω), from the transceiver over a rectilinear planar aperture. If the sampled data is available with only one or the other of the real component (I) or the imaginary component (Q), the remaining component may be derived from the sampled data using the Hibert Transform as discussed in D. Slater NEAR FIELD ANTENNA MEASUREMENTS, Artech House, Boston, Mass., 1991.

2. Perform 2-D FFT of this data with respect to x and y to obtain S ($k_x$, $k_y$,ω).

3. Multiply by a phase-factor (back-propagator) which spatially shifts the data so that is starts at the correct depth.

$$S(k_x,k_y,\omega)\, e^{-jk_zZ_1}|_{k_z=\sqrt{4(\omega/c)^2-k_x^2-k_y^2}} \quad (12)$$

4. Interpolate this data onto uniformly sampled ($k_x$, $k_y$, $k_z$) grid from the uniformly sampled ($k_x$, $k_y$,ω) data.

$$F(k_x,k_y,k_z) = (k_x,k_y,)\, e^{-jk_zZ_1}|_{=\frac{c}{2}\sqrt{k_x^2+k_y^2+k_z^2}} \quad (13)$$

5. Perform the 3-D inverse FFT.

$$f(x,y,z) = FT_{3D}^{-1}[F(k_x,k_y,k_z)] \quad (14)$$

6. Compute the magnitude of the image data.
7. Render/display the image.

WIDEBAND HOLOGRAPHIC SYSTEM

Figure 1B:
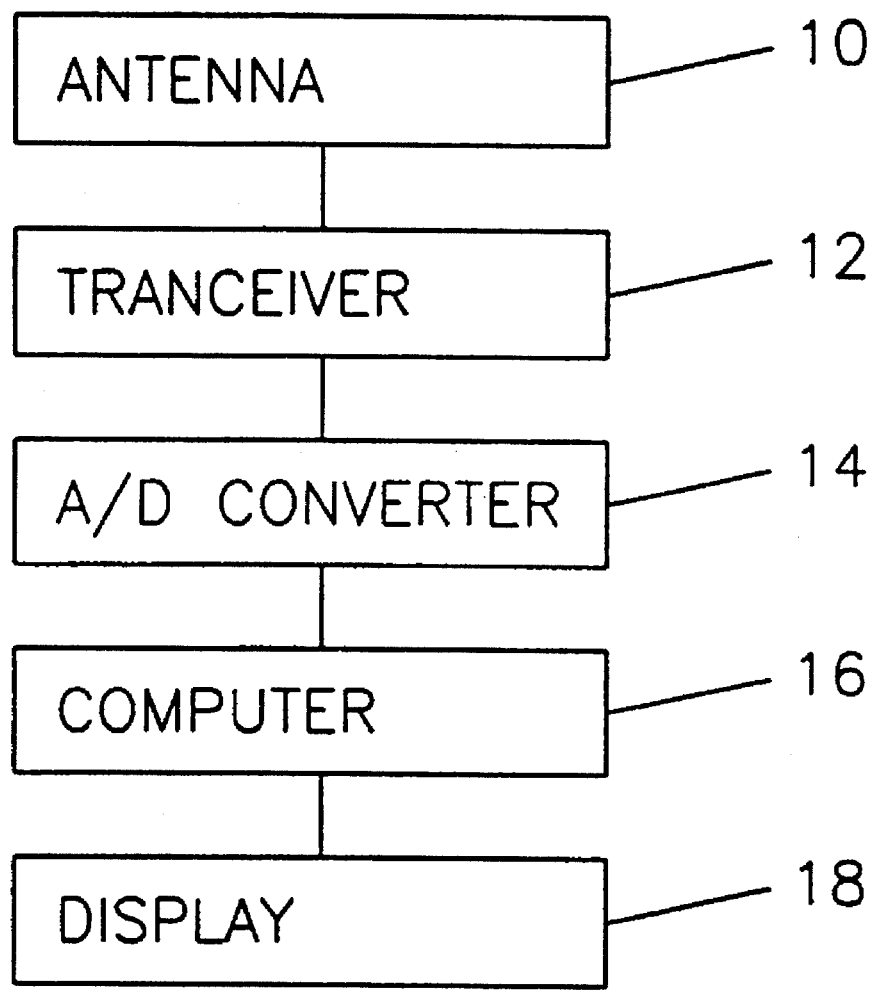
FIG. 1b is a block diagram of a holographic system.

The wideband holographic system (FIG. 1b) is made up of an antenna (10), transceiver (12), A/D converter (14), computer (16), and display (18). For a wideband system, the antenna (10) may be a single transmit/receive antenna element that is moved across a two-dimensional aperture. It is preferred, that the antenna (10) be an array of antenna elements that is at least a single row of a plurality of antenna elements. Alternatively, antenna elements may be arranged so that one row is a set of transmit antenna elements and a second row is a set of receive antenna elements. Separate transmit and receive antenna elements are preferred for a wideband system to avoid the need of a multi-frequency circulator.

It is important to recognize that simply converting a single frequency holographic transceiver to a wideband transceiver is difficult because key components, for example a phase shifter, are made to operate at a single frequency. Moreover, when using a single frequency, it is necessary to measure both the real and imaginary components of the reflected target signal. When using a wideband system, however, it is only necessary to measure the real component of the reflected target signal because there is sufficient information to permit derivation of the imaginary component. Accordingly, the transceiver is configured differently for the wideband system as compared to a single frequency system.

COMPUTER INSTRUCTIONS

The steps of the reconstruction algorithm reside on the digital computer as (i) a first set of instructions for receiving data from the A/D converter, (ii) a second set of instructions for computing a two-dimensional Fourier transform of the received data for each frequency, (iii) a third set of instructions for multiplying the two-dimensional Fourier transform by a complex backward wave propagator and forming a backward wave product, (iv) a fourth set of instructions for interpolating the backward wave product onto a uniformly sampled grid and forming an interpolated product, (v) a fifth set of instructions for computing a three-dimensional inverse transform of the interpolated product and obtaining a complex three-dimensional image, and (vi) a sixth set of instructions for computing a magnitude of the complex three-dimensional image and obtaining a three-dimensional image, and (vii) a seventh set of instructions for displaying the three-dimensional image.

ANTENNA

Figure 2A:
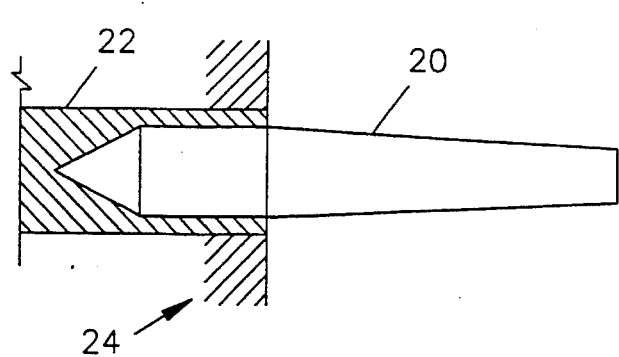
FIG. 2A is a side view of a polyrod antenna element.
Figure 2B:
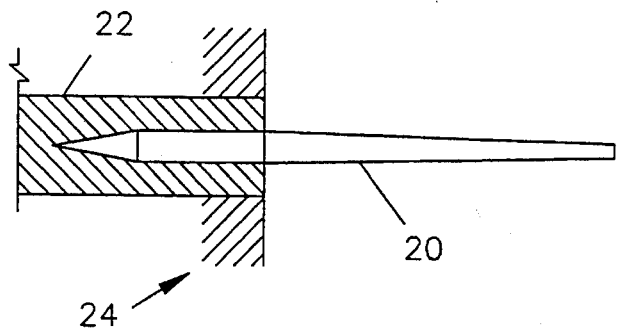
FIG. 2B is a top view, of the polyrod antenna element.

The type of antenna element may be any type including but not limited to slot line, patch, endfire, waveguide, dipole, or any combination thereof. A preferred antenna element is a polyrod antenna element (20) as shown in FIGS. 2A and 2B. FIG. 2A is a side view, and FIG. 2B is a top view, of the polyrod antenna element (20). The polyrod antenna element (20) is mounted in a waveguide (22) on an antenna base (24).

Figure 3:
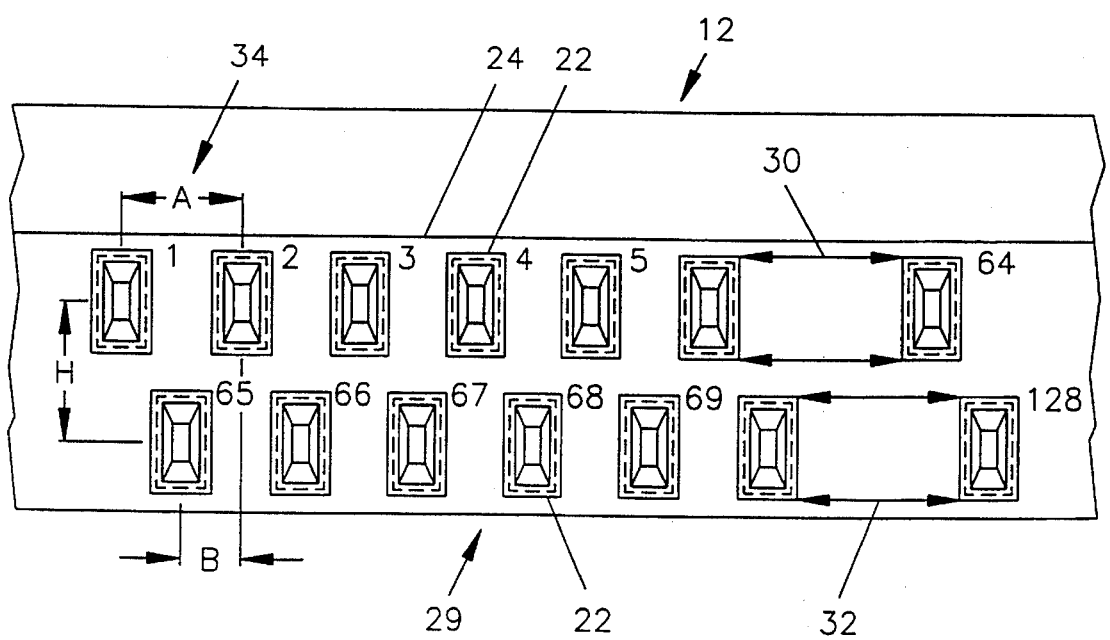
FIG. 3 shows the arrangement of the waveguides on the front of the antenna array.

The antenna elements (20) can be of any length, however, the ones used herein were four wavelengths long (at 35 GHz). Length of the antenna element (20) is determined by the selected antenna gain and bandwidth. An array (29) of antenna elements (20) is shown in FIG. 3. Signals are transmitted from a transmit antenna array (30), and reflected signals are received by a receive antenna array (32). The receive-row switched antenna array (32) is identical and is placed back-to-back with the transmit array (30). Spacing of antenna elements (20) is critical to the operation of the wideband system. To meet the Nyquist sampling criteria, an aperture must be sampled at least every one-half wavelength. In a preferred embodiment, the sampling in the horizontal dimension is fixed by the array spacing between elements. (See FIG. 3, where space A 34 between channels 1 and 2 is the array spacing). This spacing in the present system is two-thirds of a wavelength and therefore does not precisely meet the Nyquist sampling criteria. However, this spacing was chosen as a compromise between the antenna gain and beam width, possible aliasing in the imaging due to under sampling of a high spatial frequency target, and mutual coupling problems between antennas. The spacing 34 may be varied between about 0.25 to about 3 wavelength with the optimum dimension being easily chosen for a particular frequency, and application by those skilled in the art.

The antenna unit array 29 uses waveguide (WR-28) for the KA-band, 26.5–40 GHz, arranged so the waveguide ends form two 64-antenna rows at the antenna end with the orientation and spacing shown in FIG. 3. Waveguide up to and including the W-band can be used. An antenna unit is the minimum necessary to send and/or receive millimeter wave radiation. In a monostatic system as shown, an individual antenna is an antenna unit. In a bistatic system, two individual antennae form an antenna unit with a first individual antenna sending millimeter wave radiation, and a second individual antenna receiving the reflection signal. In a bistatic system there is greater sensitivity because of greater isolation between transmitter and receiver compared to a monostatic system, thereby permitting the target to be further from the antenna and still obtain a high resolution image. The antennae used are low-gain, end-fired antennae. Low-gain, end-fired antennae include but are not limited to polyrod antenna, printed circuit antennae, and other tapered slot antennae.

FIG. 3 shows the arrangement of the upper and lower antenna array 30, 32 on the front of the antenna array 29. Waveguide spacing dimensions are given for 35 GHz. These dimensions can be varied within the limits of frequency and desired resolution of the obtained image. To obtain the best possible resolution of the final image, the waveguides need to be as close together as possible. In addition to using closer antenna spacing, resolution of the image can also be increased by operating at higher frequencies. Higher frequencies than the W-band are contemplated in the invention and would of course provide even greater resolution. For example, to obtain the tightest possible grouping at 35 GHz, without physical interference of the waveguides, the vertical spacing H is about 1½ wavelengths, while the horizontal spacing A is about 1⅓ wavelengths. The upper antenna array 30 and lower antenna array 32 are offset by distance B which is preferably ½λ. The polyrod antenna 20 fit into the waveguides 22. Individual channel numbers (1-128) are noted next to the upper and lower waveguides 22.

In both the single frequency system and the wideband system, the beam width of the polyrod antenna element 20 determines the lateral resolution (f-number) of a linear holographic surveillance system. To increase lateral resolution, the beam width of the polyrod antenna 20 must be increased. It is preferred that the beam width and distance to the target result in low f-numbers, preferably between about 0.1 to about 10, and most preferably from about 1 to about 3. Antenna beam width may range from about 10 degrees to about 180 degrees. It is preferred that the beam width of the antenna range from about 10 degrees to about 50 degrees, and it is most preferred that the beam width be about 30 degrees. By increasing the antenna beam width, the gain of the antenna is decreased; however, this decreases sensitivity to reflected target signals. In addition, increasing the antenna beam width can create mutual coupling problems between antennas in linear and two dimensional holographic arrays. Mutual coupling problems can degrade the image quality. Typically, the polyrod antenna beam width is chosen so that the highest spatial frequency that can be captured in a holographic detection system is one wavelength.

The maximum number of antenna elements is determined by the frequency of the array and the array width, or area to be covered. The higher the frequency the more elements may be incorporated since the major limitation on increasing the number of elements is basically the size of the waveguide. In FIGS. 2 and 3 this limitation is readily apparent by the waveguide spacing. Here it is seen that the individual antenna are sized to fit directly in the waveguide and thus the waveguide size is the limitation on the array. The higher the number of elements for a given area, the greater will be the resolving power of the device. This is of course limited by the wavelength of the millimeter waves used. In order to obtain higher frequency operation, waveguide and/or antenna fabricated by techniques such as those for microstrip patch antenna that allows closer spacings are contemplated. For example, as a rule of thumb, the resolving power of a detection system is about one wavelength, although theoretically one would expect it to be one-half the wavelength. Thus, at 26.5 GHz the resolution is limited to about 1.13 cm (theoretical is 0.57 cm), while at 110 GHz the resolution is limited to about 0.27 cm (theoretical is 0.14 cm).

As will be appreciated by those skilled in the art, the antenna array could also be arranged so as to be mechanically scanned horizontally, circularly, or to be arranged as a two-dimensional array and have sufficient antenna placed so as not to require mechanical scanning. If desired, two or more antenna arrays could be arranged so as to scan any of the four vertical or two horizontal geometric planes of a subject; i.e., sides, top, and/or bottom. One or more additional scanners are useful since the millimeter waves do not penetrate the human body like X-rays, and therefore only one surface of the body is revealed during a scan.

TRANSCEIVER

For holography, both the magnitude and the phase of the scattered signal need to be measured. The transceiver (12) is a microwave circuit that generates a wideband signal with a voltage controlled oscillator (VCO) and sends the wideband signal to the antenna (10), through space to a target, and subsequently receives (measures) the scattered signal from the target at each of the frequencies in the wideband signal. A wide variety of transceiver designs will accomplish this task.

The transceiver (12) can be monostatic, connected to a single antenna for transmit and receive, or it can be bi-static, connected to separate antennas for transmit and receive. The transceiver (12) may be homodyne or heterodyne. Further, the transceiver (12) may produce quadrature output or in-phase output. The combination of three elements each having a pair of options results in eight possible basic transceiver designs. Electronic components of the transceiver (12) include oscillators, balanced mixers, low pass filters and amplifiers.

The received millimeter-wave frequency signal must be down-converted to a low frequency (baseband) prior to sampling by the A/D converter (14). This may be accomplished with a homodyne configuration in which the received signal is mixed with the transmit signal to obtain the baseband signal (I) which is a measure of the product of signal amplitude with the cosine of the round-trip phase to the target. For greater sensitivity, a heterodyne design can be used in which a second oscillator is used to down-convert the received signal to an intermediate frequency for amplification prior to down-conversion to the baseband frequency. In addition, the quadrature signal (Q) can also be measured by the transceiver, rather than derived from the in-phase (I) measurement.

Figure 4A:
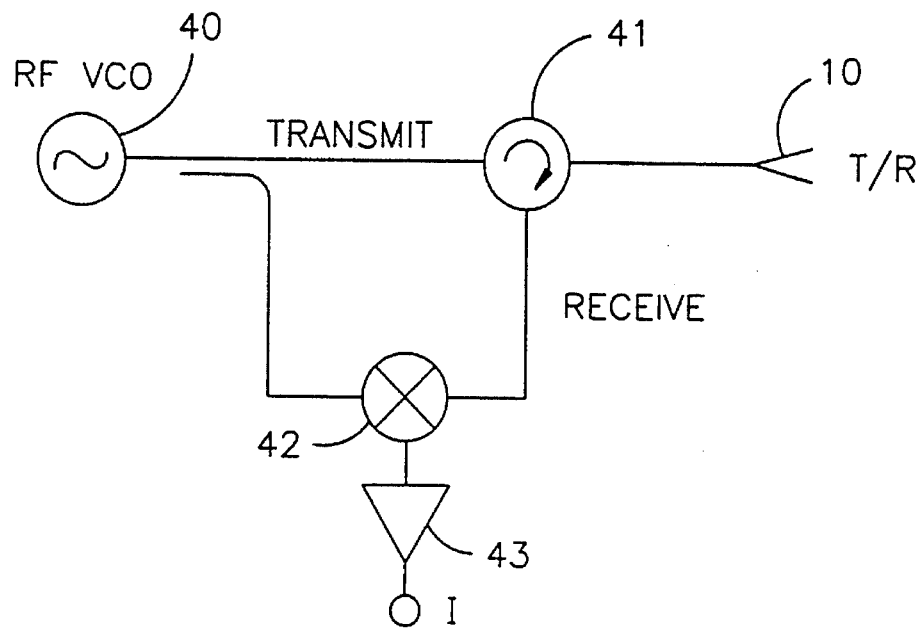
FIG. 4a is a schematic of a monostatic, homodyne, in-phase transceiver.

An example of a simple transceiver design is shown in FIG. 4a. This circuit is a monostatic, homodyne system. The transmitted signal from the RF VCO (40) is passed by the circulator (41) (or directional coupler) to the antenna (10) where it is radiated. The antenna (10) also receives the scattered signal which is routed to the receive path by the circulator (41) (or directional coupler). The mixer (42) down-converts the received signal to the baseband frequency to obtain the in-phase (I) data. The amplifier (43) serves both to enlarge this signal and to filter out the high-frequency products from the mixer (42).

Figure 4B:
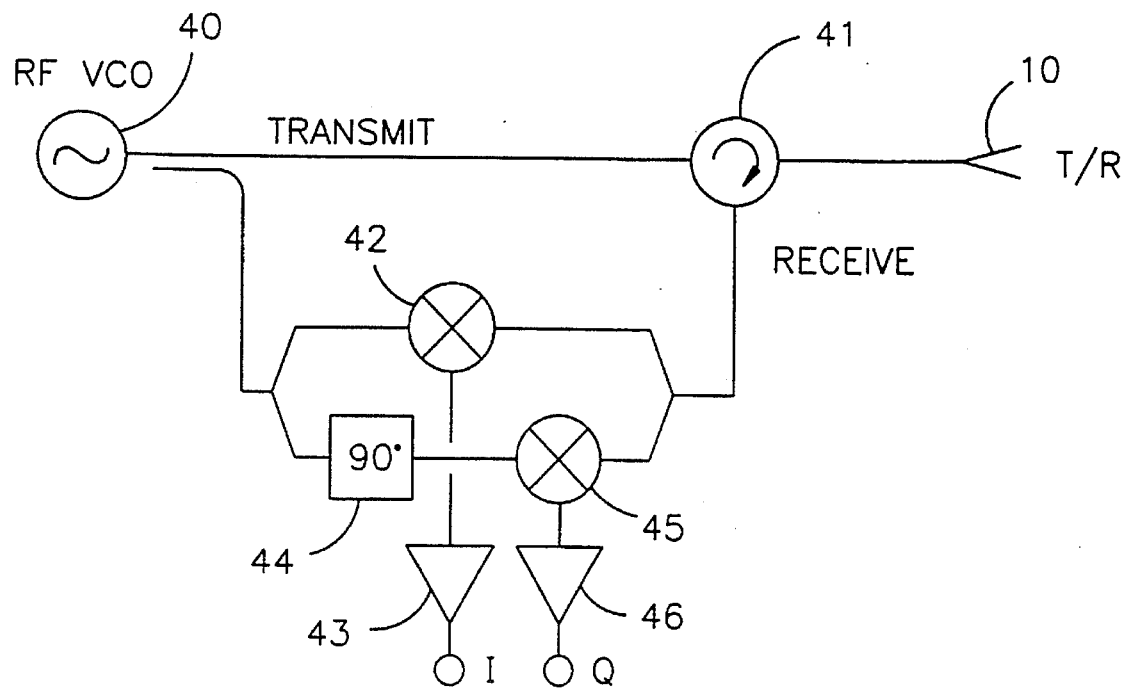
FIG. 4b is a schematic of a monostatic, homodyne, quadrature transceiver.

The quadrature (Q) data may be derived from the in-phase (I) data using the Hilbert Transform, as discussed above. In some cases, it is desirable to measure both the in-phase (I) and quadrature (Q) signals directly with the transceiver. This is referred to as full-quadrature outputs. An example of a homodyne, monostatic, full-quadrature transceiver is shown in FIG. 4b. In this transceiver (12), the in-phase (I) signal is obtained in exactly the same manner as in FIG. 4a. The quadrature signal is obtained by phase-shifting the RF VCO signal by 90 degrees in the phase-shifter (44) prior to mixing with the received signal in a separate mixer (45), and amplifying in a separate amplifier (46). This signal is also down-converted to baseband but represents the amplitude times the sine of the round-trip phase to the target and is the quadrature (Q) signal.

Figure 4C:
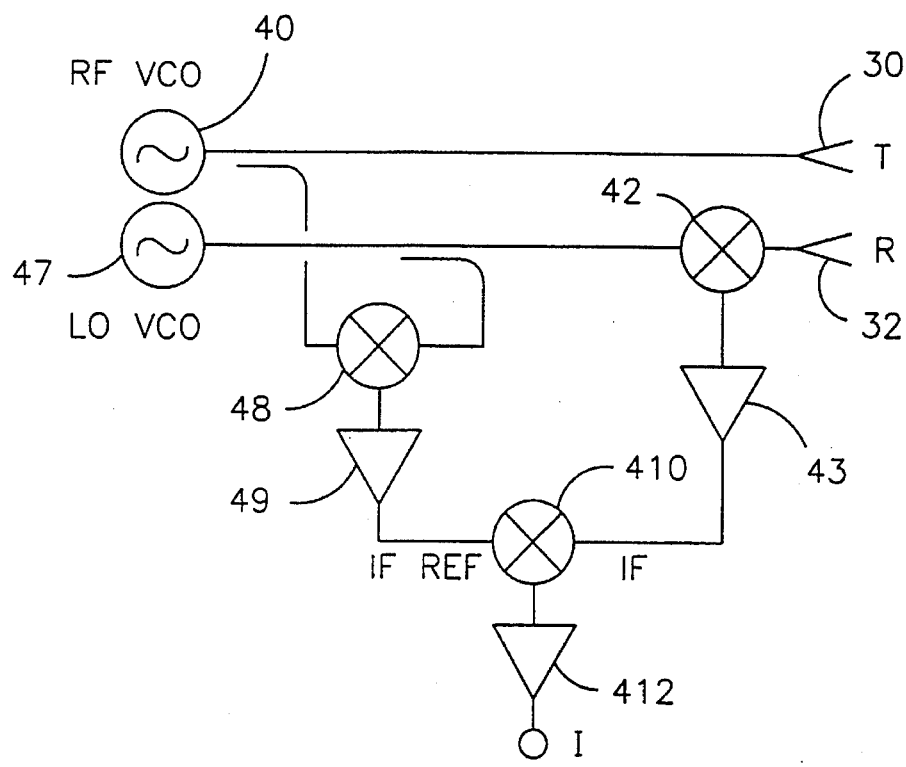
FIG. 4c is a schematic of a bistatic, heterodyne, in-phase transceiver.

For improved sensitivity, the transceiver (12) may incorporate a heterodyne configuration rather than the homodyne configuration. In a heterodyne system, the received signal is down-converted first to an intermediate frequency (IF) where it is amplified and filtered prior to the final down-conversion to the baseband frequency. An example of a bi-static, heterodyne, in-phase only transceiver is shown in FIG. 4c. In this transceiver (12) the RF VCO (40) wideband signal is transmitted directly by the transmit antenna (30). The received signal received by the receive antenna (32) is mixed with another oscillator (47) to down-convert the received signal to the intermediate frequency (IF). The LO VCO oscillator (47) is offset in frequency from the RF VCO oscillator (40) by the IF frequency. To maintain phase coherence an IF REF signal is obtained by mixing the RF VCO and LO VCO signals in a mixer (48). This signal is amplified and filtered in the amplifier (49) to remove higher frequency mixing products. Mixing the IF and IF REF signals in the final mixer (410) yields the in-phase signal (I). A final amplifier (412) may be used to increase the in-phase signal (I) strength.

Figure 4D:
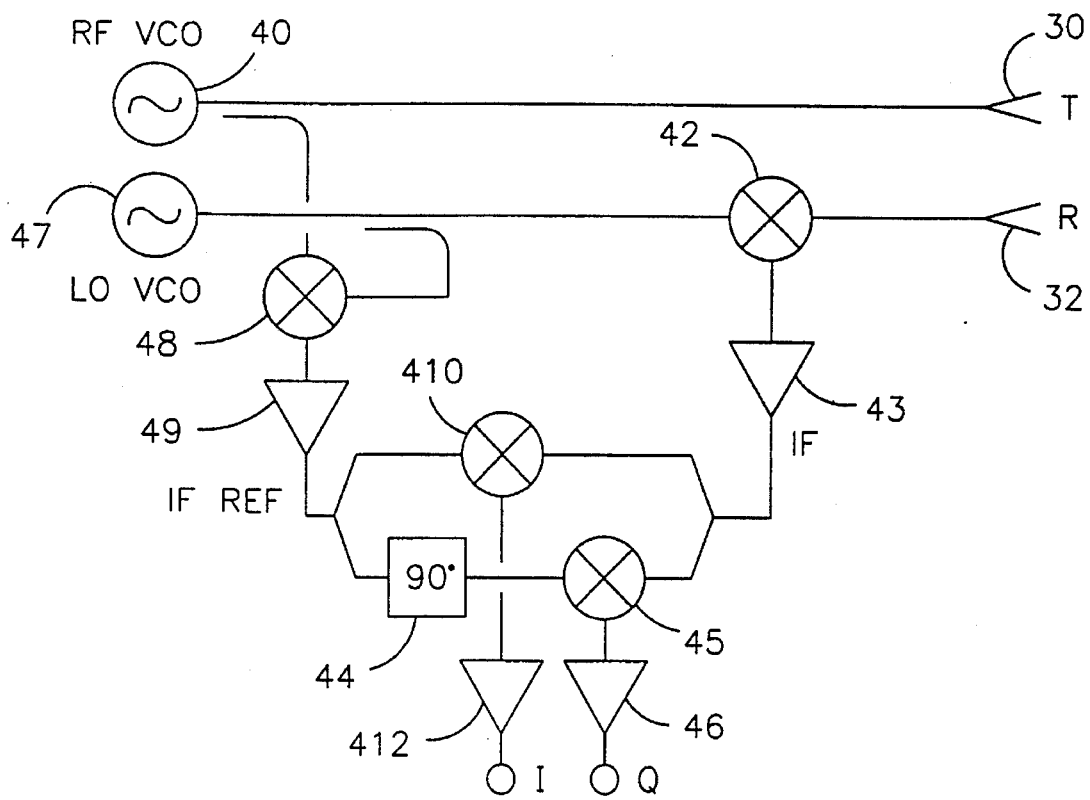
FIG. 4d is a schematic of a bistatic, heterodyne, quadrature transceiver.

The transceiver (12) of FIG. 4c may be modified to yield full-quadrature outputs, as shown in FIG. 4d. This transceiver (12) is a bi-static, heterodyne, full-quadrature design. The in-phase (I) signal is obtained in exactly the same manner as in FIG. 4c. The quadrature signal is obtained by phase shifting the IF REF signal by 90 degrees in the phase-shifter (44) prior to down-converting to baseband in the separate mixer (45) to obtain the quadrature (Q) signal.

Although only four of the eight basic possible designs have been shown and described, it will be apparent to those skilled in the art of holographic transceiver design that many other variations are possible, including measuring only quadrature data (Q) and deriving in-phase data (I) using the Hilbert transform. It will be further apparent that FIGS. 4a–4d show only the critical components. Additional components including but not limited to amplifiers, filters, frequency doublers and attenuators, may be added to an actual design depending upon the operation/performance of particular components and the desired output from the transceiver (12).

Figure 4E:
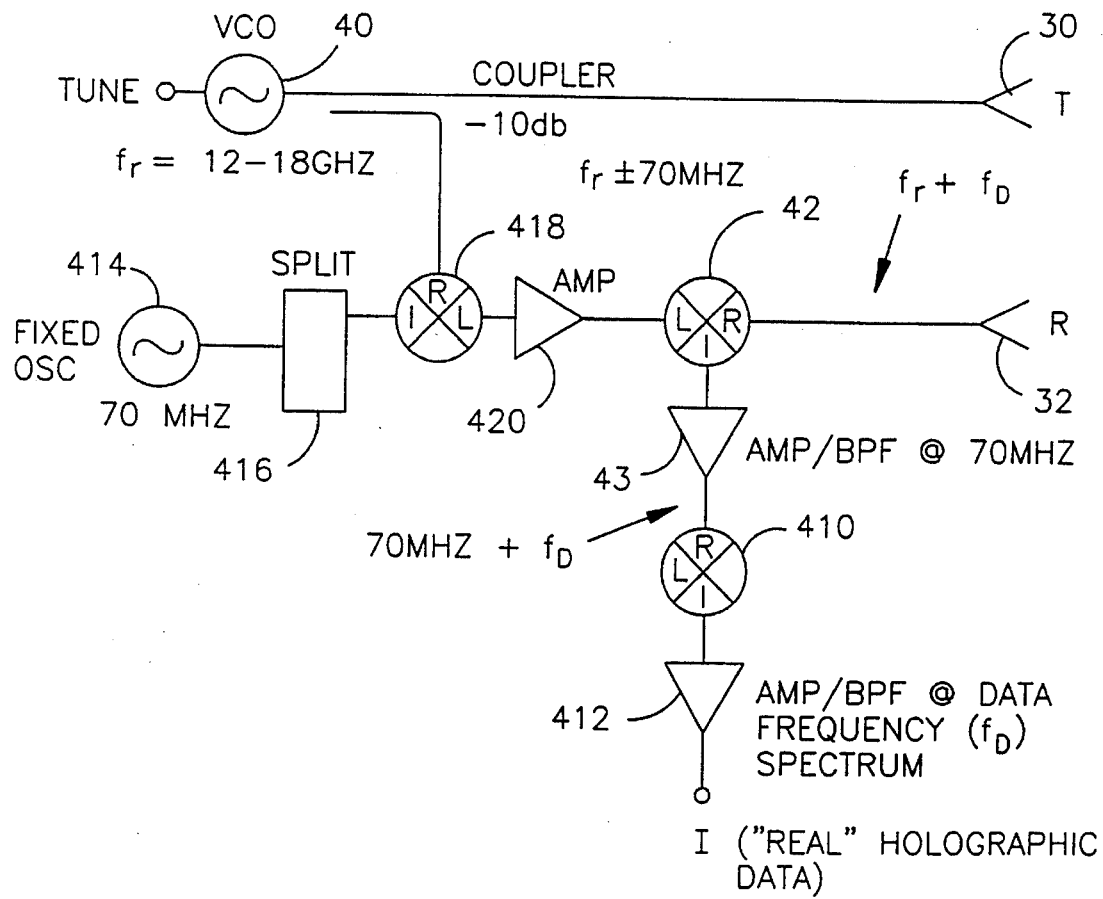
FIG. 4e is a schematic of a bistatic heterodyne, in-phase transceiver with a single VCO.

One of the possible variations is shown in FIG. 4e. Rather than sweep a second microwave VCO (47) as in FIGS. 4c and 4d to set the IF, a fixed oscillator (414) (for example 70 MHz) is used that is independent of the VCO (47). The output from the fixed oscillator (414) is divided by a splitter (416), preferably a CMOS. A first portion of the split signal is mixed with a portion of the output from the VCO (47) in a mixer (418). The output from the mixer (418) is sent through an amplifier (420) prior to entering the receive signal mixer (42). A second portion of the split signal is directed to the final mixer (412). The advantages of replacing the VCO (47) with the fixed oscillator (414) include (1) reduced hardware cost since a fixed oscillator is much less expensive than a VCO, and (2) eliminates the need for coordinating tracking between two VCO's for the desired IF. More specifically, linearizing and matching tasks are eliminated. A further advantage is removal of noise from frequency variance that occurs when dual VCO's are used. This transceiver is referred to herein as a bistatic, heterodyne, in-phase, non-tracking transceiver, where non-tracking refers to the VCO/fixed oscillator combination.

Figure 5:
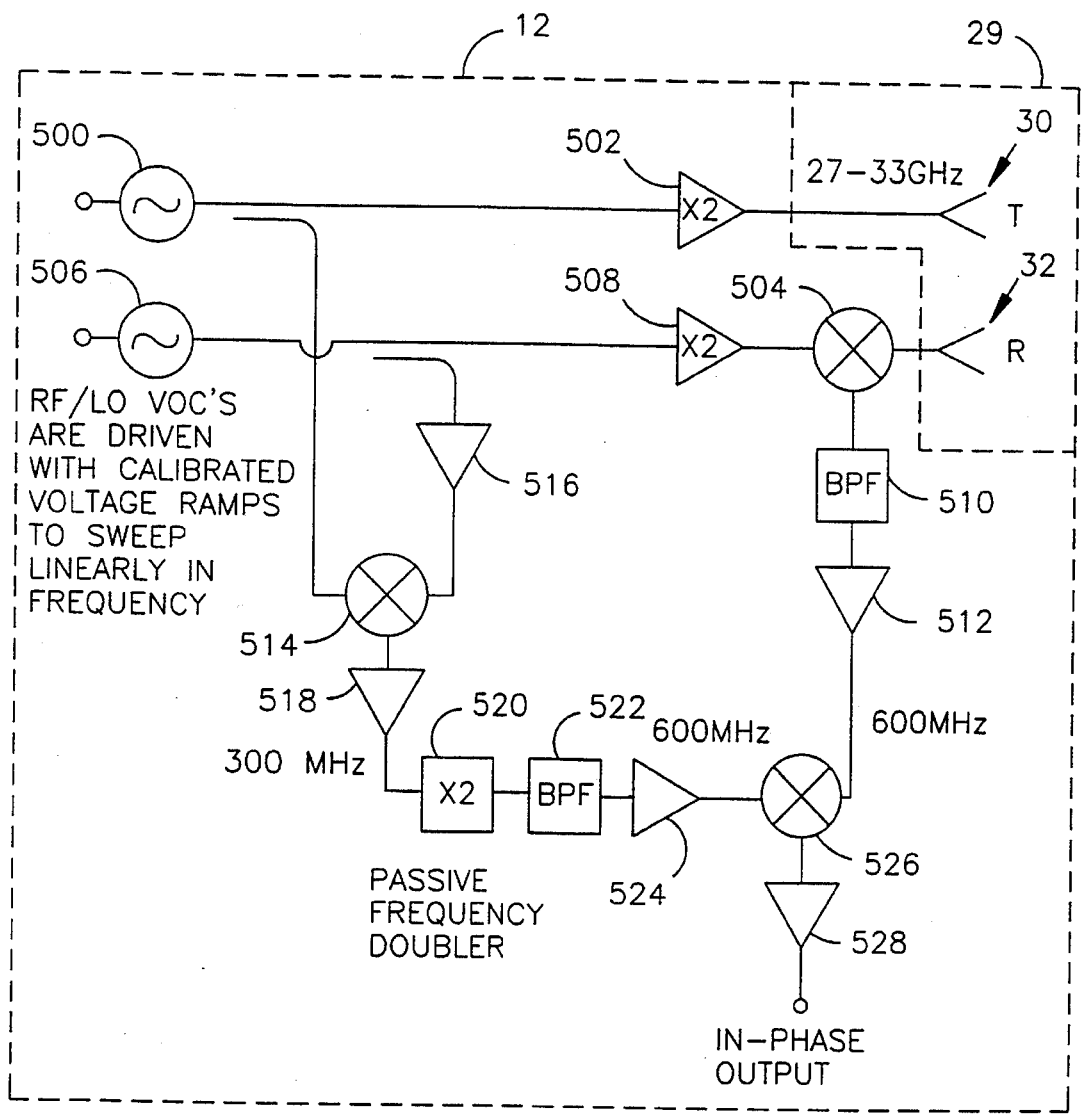
FIG. 5 is a schematic of a preferred bistatic, heterodyne, in-phase transceiver.

A preferred embodiment of transceiver (12) is shown in FIG. 5. This transceiver (12) is a bi-static, heterodyne, in-phase transceiver, similar to FIG. 4c. A first wideband oscillator (500), for example RF VCO 13.5 to 16.5 GHz, sends a signal through an active frequency doubler (502), and the signal is transmitted via a transmit antenna array (30). Reflected radiation is received via a receive antenna array (32). The received signal is combined with a second oscillator signal in a receive signal balanced mixer (504). The second oscillator signal is produced by a second wideband oscillator (506), for example LO VCO 13.2 to 16.2 GHz, and an active frequency doubler (508). The low frequency portion of the combined receive signal is retained through a low pass filter (510), and amplified in a receive signal amplifier (512). Simultaneously, reference signals from the oscillators 500, 506 are combined in a reference signal balanced mixer (514). The reference signal from the second wideband oscillator (506) is amplified by amplifier (516) prior to combining with the reference signal from oscillator (500). The combined reference signal is amplified through amplifier (518), doubled in an passive frequency doubler (520), then passed through a low pass filter (522), and a second reference amplifier (524). The combined reference signal and the combined receive signal are further combined in a final balanced mixer (526) providing a baseband signal that is amplified in an output amplifier (528) to produce an in-phase output.

In operation, the oscillators (500, 506) are voltage controlled and are driven by calibrated voltage ramps, so that their output frequency responses are approximately linear. The LO oscillator (506) is calibrated to track the RF (transmit) oscillator (500) offset by approximately 300 MHz. Both the oscillators (500,506) are frequency doubled to produce approximately 20 mW in the 27 to 33 GHz frequency band. A 600 MHz intermediate frequency combined reference signal is obtained by mixing reference signals from the oscillators (500,506) prior to transmission of the RF signal and subsequently frequency doubling the signal. The 600 MHz combined received signal is obtained by mixing the received version of the transmit signal with the LO oscillator (506). The combined reference signal and the combined receive signal are further combined providing a baseband signal that is amplified to produce an in-phase output. The in-phase output signal is proportional to the cosine of the round-trip phase to the target which is the data necessary for reconstruction using the algorithm previously described.

TRANSCEIVER SWITCHES

Millimeter-wave switching is required in the wideband holographic imaging system in order to provide high-speed sampling of the two-dimensional aperture. Under high-speed electronic control, each antenna element (20) must be individually connected to the transceiver (12). For a small number of antenna elements (20), the switching connections are simple and may be accomplished with off-the-shelf single pole double throw (SPDT) switches. However, as the number of antenna elements (20) increases, even to the modest amount of 64, the size of the transceiver (12) is affected by the number of switches and branches in a binary switching tree. Accordingly, a compact switch was made for the transceiver (12).

In the present invention, a binary tree switch structure is used in which the overall switch array is composed of single-pole double-throw (SPDT) switch elements. In this structure, the input is fed into a SPDT module which in turn drives 2 SPDT modules. The four outputs of these two SPDT elements will then drive 4 SPDT elements, and so on, until the desired number of outputs is obtained. The switched linear array is composed of two 64 element arrays, which each require 6 layers of SPDT elements for a total of 63 SPDT elements in each array. It is possible to construct an array using commercially available SPDT pin-diode milli-meter-wave waveguide switches, however, this array would be very bulky, and it would be difficult to arrange the outputs to have the desired spacing.

To overcome this difficulty, a custom single-pole 8-throw (SP8T) switch module (FIG. 6, 600) was designed and fabricated specifically for this application. Internally, the SP8T switch module (600) uses a binary tree structure composed of three layers of SPDT switch elements for a total of 7 SPDT elements. The SP8T module is constructed of aluminum using a split-block waveguide structure. Each SPDT element contains a duroid fin-line printed circuit junction which uses shunt pin-diodes to direct the millime-ter-wave signal to the desired output waveguide. The pin-diodes are controlled by electronic driver circuitry mounted in a housing on top of the split-block.

Figure 6:
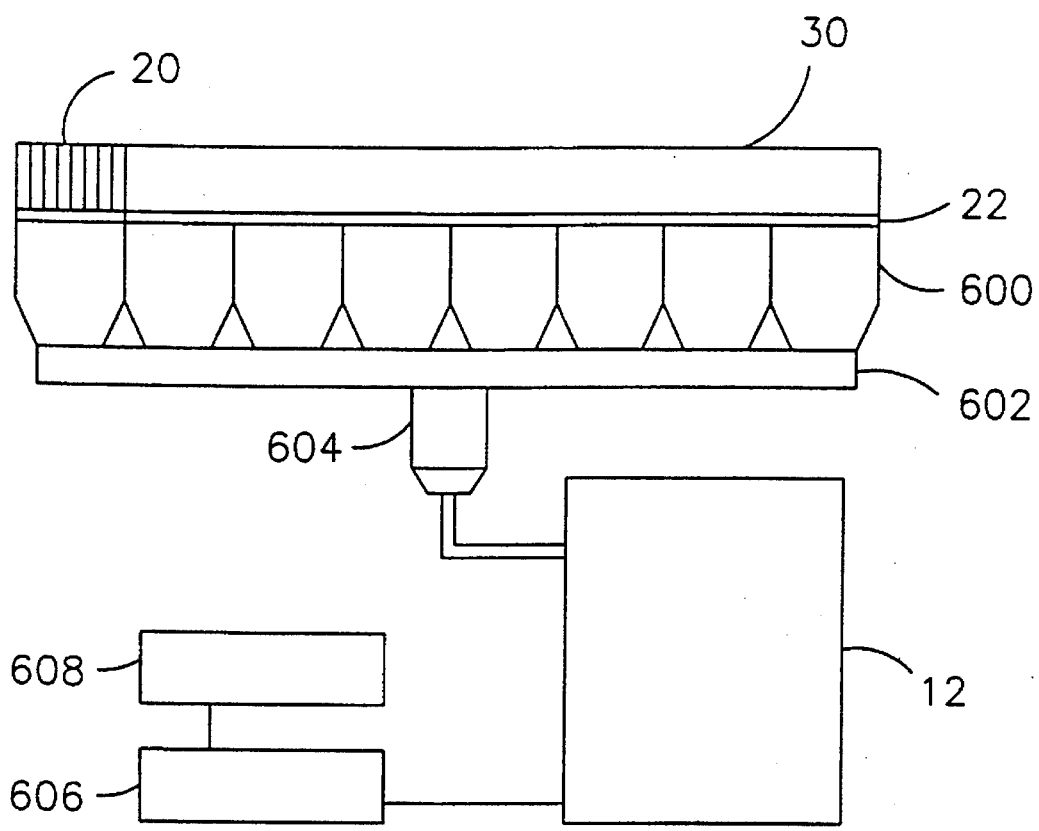
FIG. 6 is a diagram of a switch array.

As shown in FIG. 6, the transmit antenna array (30) having 64 antenna elements (20) is interconnected to 8 single-pole eight-throw (SP8T) pin-diode waveguide switches (600) with a waveguide manifold feed (602) and fed by a ninth SP8T waveguide switch (604). Two of these arrays then form the complete transmit and receive array assembly.

Each of the 64 outputs has a small polyrod antenna element (20) inserted into the waveguide (22). Integrated switch drivers are contained within each SP8T switch (600, 604), allowing a simple connector with power and coded logic inputs to each of the 18 SP8T switches (600, 604). The transceiver (12) provides the swept wideband millimeter-wave source to the transmit-array (30) for subsequent illu-mination of the target (not shown) through the electronically selected transmit channel. The transceiver (12) also provide the local-oscillator (LO) millimeter-wave signal for down conversion of the received signal through the selected receive antenna.

While a binary switching means has been described above, other switching means such as, for example, a comb-type transmission-line-sequential switching array with appropriate wiring and control adjustments can also be used.

Interference between the incoming signals and outgoing signals is prevented, and improved separation attained by transmitting on one channel and simultaneously receiving on another channel (bi-static). Further, while it is possible to operate both the transmit and receive antenna arrays with all antenna elements (20) on, it is preferred to sequentially transmit across the upper sixty-four channels (numbers 1–64 in FIG. 3) of the upper antenna array 30, while simulta-neously sequentially receiving return signals with the lower sixty-four channels (numbers 65–128 in FIG. 3). Thus, when transmitting through upper antenna channel 1 with the first binary switch array, signals are simultaneously received through the lower channel 65 with the second binary switch array. When transmitting with upper channel 2, reception is through the lower channel 66, and so on. Sequential trans-mission results in improved resolution for a given antenna spacing.

OTHER COMPONENTS

The VCO DRIVERS board (606) provides the electronics to generate the tuning voltages to the transmit voltage-controlled oscillator (VCO) and the local-oscillator (LO) VCO. The ARRAY-CPU INTERFACE board (608) provides the switch logic necessary to sequentially switch through each of the 127 effective sampling points, and provides the communications link to and from the controlling computer.

The wideband system preferably operates in the K-a frequency band (26.5 to 40 GHz). The wideband system that has been assembled operates from 27 to 33 GHz. There are 128 antenna elements organized as an upper-row (30) of 64 transmit antennas (20), and a lower row (32) of 64 receive antennas (20). Logic circuitry in the ARRAY-CPU INTER-FACE board 608 sequences the transmit and receive anten-nas to transmit from one antenna and receive the reflected signal from each of the two nearest neighbor antennas in the receive row. This places a virtual sampling point halfway in between each transmit and receive antenna. The transmit row (30) and receive row (32) are preferably offset by half the antenna spacing, so the effective sample spacing is one-half of the single-row antenna spacing. This sequencing scheme cannot be used on the last antenna element, so the effective number of sample points for a 128 antenna element array is 127. The horizontal aperture width is 72.6 cm which yields an effective sample spacing of 5.7 mm.

The wideband data is sampled horizontally across the array and vertically over the aperture and is digitized by an Analog to Digital converter (A/D) (14) for subsequent storage in the computer. After digitizing, the reconstruction algorithm discussed in the previous section is applied to reconstruct the three-dimensional image of the target. The three-dimensional image is then collapsed into a fully-focused two-dimensional image of the target for display on the computer.

Figure 7:
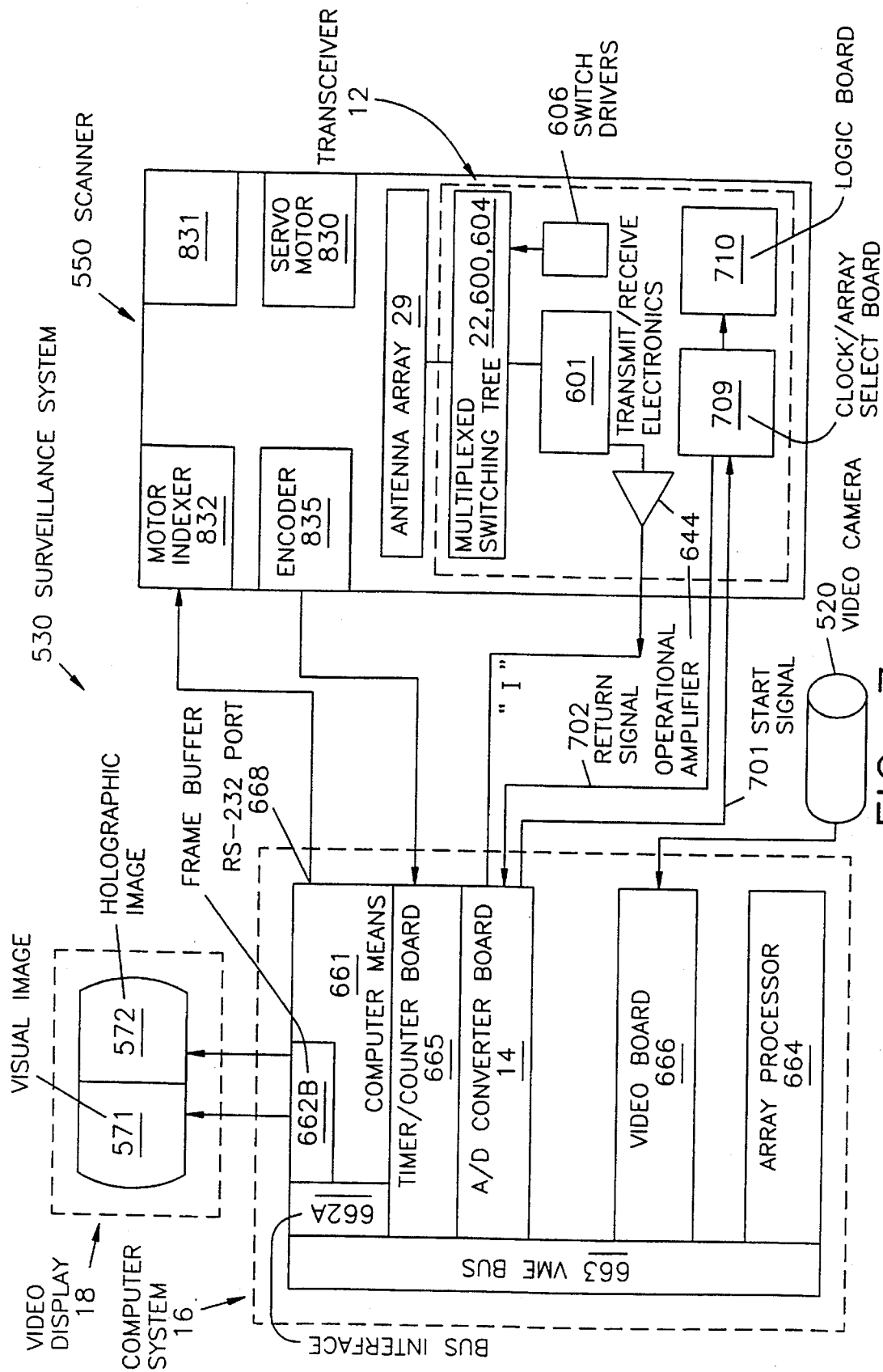
FIG. 7 shows the arrangement of interconnections of the computer and various control points in the overall system.

Refer now to FIG. 7, which shows details of the surveil-lance system 530 having interconnection of the computer system 16 with the drive system of the scanner 550 and the transceiver 12. Computer means 661, such as a Computer System SUN 4/370 GX 661, is used for control and calcu-lations for reconstruction of the holograms. This computer is a Reduced Instruction Set (RISC) computer with a bus interface 662A, a VME bus 663, and has 32 Mbytes of memory and a 670 Mbyte hard drive. An array processor 664, such as a Skybolt array processor, based on the Intel 860 & 960 chip set, having a maximum speed capability of about 80 Mflops, is used to accelerate the math operation discussed in the holographic algorithm above. A start signal 701 is sent to the clock/array select board 709 for initiating and controlling the sequence to the logic board 710. A return data valid signal 702 is used to confirm that data from the "I" channel is ready to be received by the A/D converter board 669. The logic board 710 determines which channel is "on" in the antenna array 29. The encoder 835 provides the computer system 16 the vertical position where the holographic array assembly is on the scanner 550. The computer system 16 determines when a horizontal scan is necessary and sends the start signal 701 to initiate the scanning process. The antenna array 29 is sequentially scanned to the individual waveguides 22, first through the upper antenna array 30 and then through the lower antenna array 32. The data from each channel is sent back to the computer system 16 through the multiplexed switching tree 22, 600, 604 as discussed above. After scanning through the upper and lower antenna array 29 once, the scanning is stopped and the transceiver 12 waits for the next "start" command from the computer system 16 when it is in its next appropriate vertical position on the scanner 550. If desired, scanning can be initiated at the lower array 32 rather than the upper array 30.

The A/D converter board 14 is preferably a high speed analog input board for the VME bus 663, with associated A/D software driver having a speed of at least 5 MHz and capacity of at least 8 Mbytes. It is used to capture the analog amplitude and phase information signals from the transceiver 12 and convert them to digital form. The timer/counter board 665 for the VME bus 663 is used to control the timing sequence for the transceiver 12 based on positional information provided by the encoder. The video board 666 provides a high resolution frame grabber and is used for displaying an optical picture obtained from the video camera 520 on an optional video display 18 that preferably provides a visual image 571 along with a holographic image 572 of an individual. The frame buffer 662B interfaces the computer with the video display 18 that may consist of a visual image 571, a holographic image 572, or other output means. The servomotor 830 on the scanner 550 is controlled by the motor driver 831 and motor indexer 832 that obtains control signals from the computer system 16 through the RS-232 port 668.

Figure 8A:
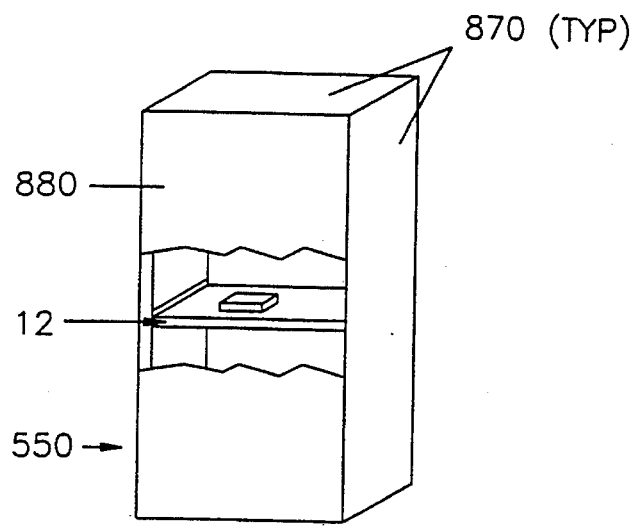
FIGS. 8a, 8b, and 8c depict an embodiment of a mechanical scanner useful in monitoring travelers at transportation centers such as airports.
Figure 8B:
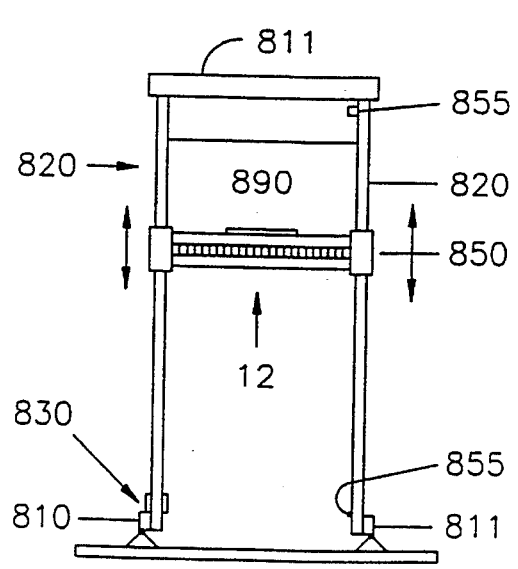
Figure 8C:
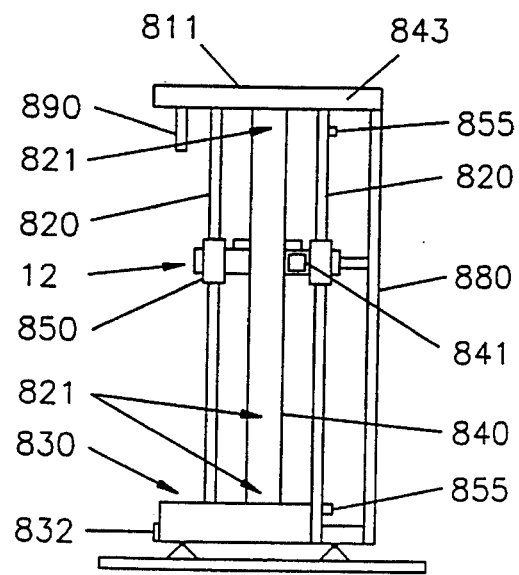

Referring now to FIGS. 8a, 8b, and 8c, in a presently preferred embodiment, scanner means such as the scanner 550 is capable of moving a transceiver 12 vertically at a distance and at a rate that allows appropriately rapid scanning of the target. The scanner 550 includes a support means such as a base 810 and upper frame 811; support beams 820; a motor drive system such as a servomotor 830 and associated controls (see FIG. 7); a belt drive system, such as belt 840, belt attachment 841, and support pulley 843; and guide 850 for slidable attachment to support beams 820. The scanner 550 is preferably constructed with panels 870 of metal or plastic to provide soundproofing and physical protection during scanner operation. The front of the scanner 550 is preferably covered with a window panel 880 fabricated from special low-loss millimeter wave window material such as Rexolite™. Other materials that can be used include low loss tangent materials such as those that are usable in radomes (e.g., Nylon, Lucite, and the like). In addition to having low loss, the materials should also be rigid. The window panel 880 should preferably not be so thick so as to substantially reduce sensitivity. At frequencies of about 110 GHz and below, it should be no more than about one wavelength thick. While FIGS. 8b–8c depict four beams 820 on which the transceiver 12 is slidably attached, it is presently preferred to use two beams with the beams between positions 821 at the center of the sides of the transceiver 12, see FIG. 8c. This reduces the chances of binding during the mechanical scan. Limit switches 855 provide control for stopping the array assembly.

Figure 9:
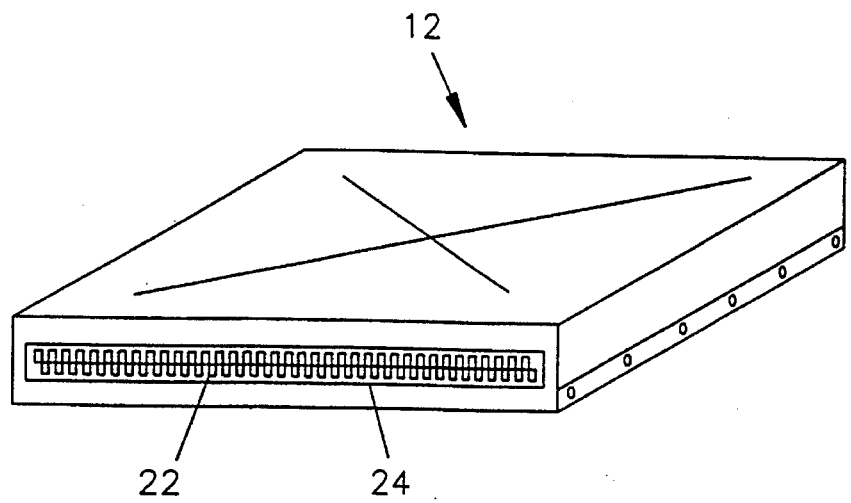
FIG. 9 shows the arrangement of the antenna elements on the antenna array.

FIG. 9 shows the general arrangement of the antenna array 24 on the front of the transceiver 12.

The scanner 550 can be operated in three modes of operation:

1. Automatic Mode:

When a scan command is sent from the computer system 16 to the logic board 710 and motor indexer 832, the transceiver 12 will scan a predetermined test aperture, stop, and wait for another command. When a second scan command is sent, the transceiver 12 will be scanned to the other end of the predetermined aperture and wait for another command. This routine can be repeated as long as scan commands are issued.

2. Calibration Mode:

Calibration Procedure for Holographic Arrays.

As is apparent to those skilled in the art, a calibration procedure to correct for offsets and phase/amplitude variations in each holographic array channel is necessary for array normalization. This calibration process forces the holographic array to appear like a single element holographic system. Without this calibration processing, holographic imaging with array technology would not be possible. When a calibration command is sent to the motor indexer 832, the calibration procedure is performed in two steps. The first step is to correct for offsets, which step is performed by electronically scanning each antenna 20 channel without a high reflective object in front of the transceiver 12, and store the offset values in the computer system 16. The stored offset values are used to force the array element offsets to the same value by appropriate calculations. The second calibration procedure is performed with a flat metal plate 890 that is perpendicular to the antenna array 29 on the transceiver 16, see FIG. 8b–8c. Each of the 128 channels has a different phase and amplitude associated with it before calibration. The flat metal plate 890 provides a standard reference in which the phase and amplitude of each channel can be calibrated. This second calibration can be performed in the computer in a similar fashion as the first.

3. Manual Mode:

The transceiver 12 can be positioned anywhere in the aperture using a manual controller. The manual controller may be part of the motor indexer 832.

The drive system is controlled by the motor indexer 832 that is interfaced to the computer by a standard interface such as an RS-232. An example is stepper or servomotors controlled by a Parker Computer C3000 indexer. Scan speed should be appropriate to the target to be examined but can vary from about one to several seconds for a mechanical scanner to milliseconds for a totally electronic scanner for a seven-foot scan aperture. An aperture scan for evaluation of human subjects at a transport facility, for example, must be fast enough so that movement of the individual does not interfere with the scanned image. While this can be accomplished with a fully electronic scanner, in the case of a mechanical scanner, depending on the speed of the scan, moving objects or living subjects will ordinarily need to remain still for the duration of the scan. It is understood that in the preferred embodiment, as the transceiver 16 is electrically scanned across its width, it is simultaneously scanned mechanically in a vertical direction. To provide good images it is preferred that one horizontal scan of both the upper and lower antenna arrays 30, 32 be complete before the antenna array assembly 29 has moved one-tenth wavelength vertically; otherwise, the phase differences across the array 29 may cause image degradation.

The electronic scan is made up of transmitting and receiving a signal from an individual antenna unit in sequence one at a time in successive order. Electronic millimeter wave switches are used to direct signals to the antenna units. An antenna unit may be a single antenna (monostatic) that both transmits the source signal and receives the reflection signal from the target. Alternatively, the antenna unit may be two antennas (bistatic) in which one antenna transmits the source signal and the other antenna receives the reflection signal from the target.

In a multi-antenna unit linear array system, the linear array may be mechanically scanned in one direction (e.g., vertical) and electronically scanned in the other (e.g., horizontal). Alternatively, in a multi-antenna unit planar array system, the array would be electronically scanned in both directions.

Materials through which the apparatus is able to scan and provide detection of concealed objects includes the low-loss tangent dielectric materials such as clothing, plastics, natural and processed plant materials (such as woven materials, wood, leather, and the like), glass, epoxies, Kevlar, and the like. With the preferred system of the invention, an individual can be inspected in less than two seconds.

Materials readily capable of detection are those whose relative dielectric constant is larger than the barrier which they are behind, provided the barrier has losses low enough to permit the signal to penetrate and return. Materials whose relative dielectric constants are lower than the barrier materials may also be detected indirectly by shadowing due to other surrounding materials having higher relative dielectric constants. When highly reflective barriers (e.g., conductors) are encountered, they can be detected and the contents behind or in them inspected manually.

Figure 10:
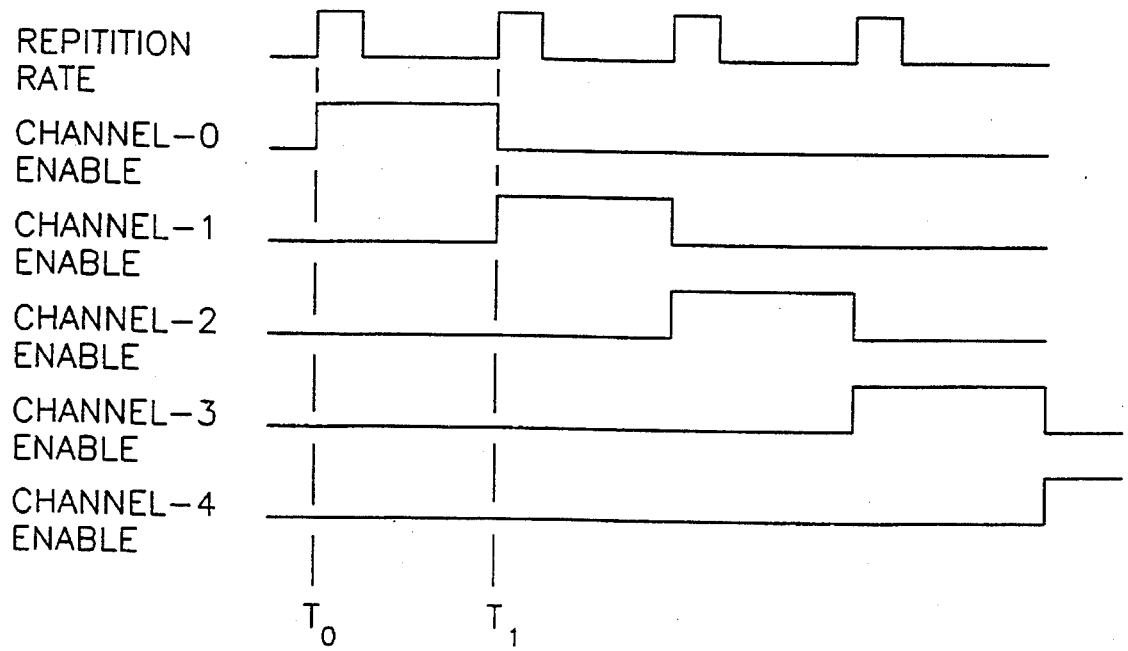
FIG. 10 shows the timing sequence for the individual channels of the multiplexed switching tree.

FIG. 10 shows the general timing sequence for an outgoing signal for the first four individual channels of the antenna array 29. Each channel should ordinarily be "on" about 10 to 20 µsec at a frequency range from about 7 to 33 GHz at the repetition rate provided by the clock. The remaining 124 channels are sequenced similarly.

Initially, single frequency systems operating at frequencies of 35 GHz and 90 GHz were demonstrated. However, systems have been found operable with frequencies ranging from about 1 GHz to about 110 GHz and above. Preferred systems operate from about 6 GHz to about 40 GHz, because frequency generators are less expensive in that range.

EXAMPLE 1

An experiment was performed to compare the image obtained with a single frequency holographic system to an image obtained with a wideband holographic system according to the present invention.

Figure 11A:
FIG. 11a shows a front view image of a person using a single frequency millimeter wave holographic system.
Figure 11B:
FIG. 11b shows a back view image of a person using a single frequency millimeter wave holographic system.
Figure 12A:
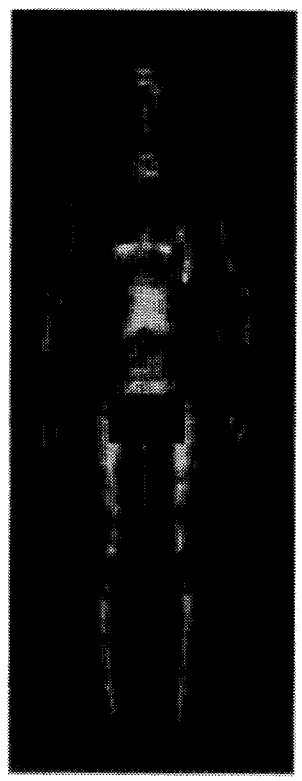
FIG. 12a shows a front view image of a person using a millimeter wave holographic system.
Figure 12B:
FIG. 12b shows a back view image of a person using a millimeter wave holographic system.
Figure 13A:
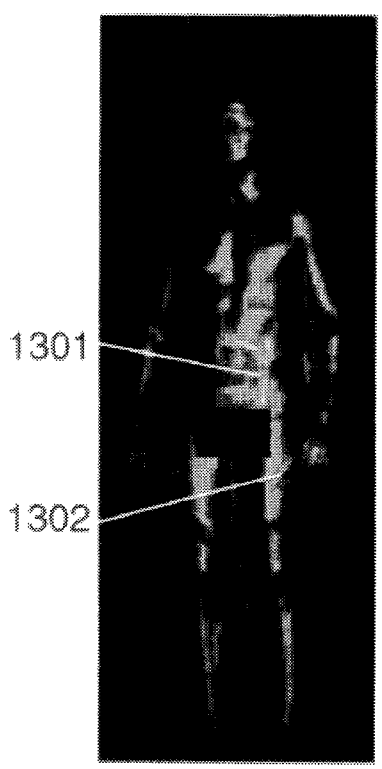
FIG. 13a–13f show wideband images of a man carrying concealed handguns along with innocuous items.
Figure 13B:
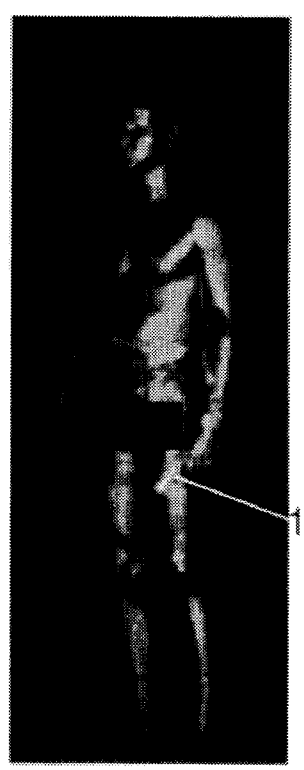
Figure 13C:
Figure 13D:
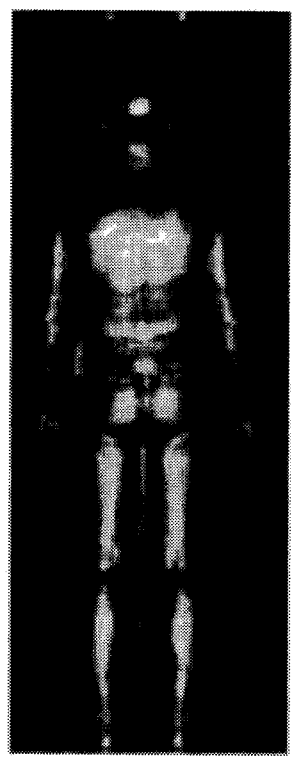
Figure 13E:
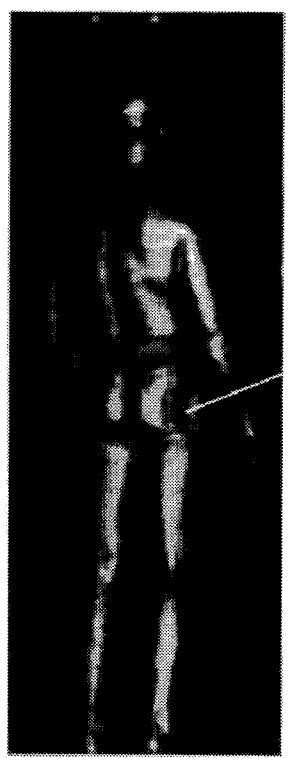
Figure 13F:
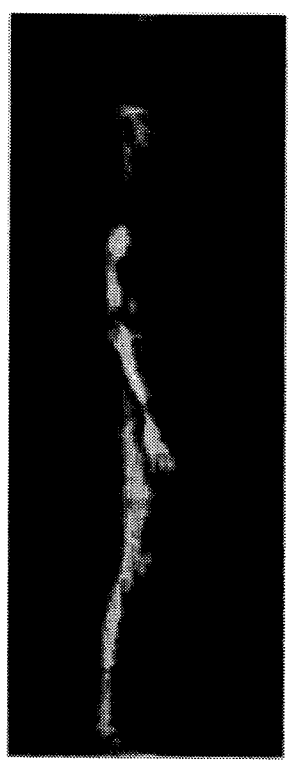

The imaging target was a person having a concealed object. FIGS. 11*a*, 11*b* and 12*a*, 12*b* show the dramatic improvement in image quality that has been obtained by converting the single frequency millimeter-wave imaging system to wideband operation. The single-frequency (35 GHz) images of FIG. 11*a* and FIG. 11*b* show significant degradation due to lack of focus over many parts of the image, especially the arms and legs. In addition, some degradation is apparent due to poor sensitivity in the single frequency transceiver. By contrast, the wideband images (27 to 33 GHz) of FIG. 12*a* and FIG. 12*b* are fully-focused due to the three-dimensional image reconstruction. Significantly higher dynamic range is also apparent in the wideband images. This is due to better focus, as well as to the very high sensitivity of the transceiver design.

EXAMPLE 2

FIGS. 13*a–f* show six wideband (27 to 33 GHz) images of a man carrying two concealed handguns (1301, 1302) as well as several innocuous items (1303, 1304). The first image (a) shows a Glock-17 handgun (1301) tucked at the beltline under the mans shirt, and a small handgun (1302) in the man's left pocket. The second image (b) also shows the small handgun (1302) in the man's left pants pocket. The third image (c) shows a vinyl/paper checkbook (1303) in the left back pocket. The fifth image (e) shows a leather wallet (1304) in the man's right back pocket.

CLOSURE

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit or scope of the invention.

We claim:

1. A holographic apparatus for near real-time imaging of a target, said apparatus utilizing millimeter wave radiation having a plurality of frequencies from about 1 to about 110 GHz, comprising:

(a) a holographic array having a plurality of antenna units spaced apart from about 0.25 to about 3 wavelength, wherein each unit sends and/or receives millimeter wave radiation, said array spaced apart from said target;

(b) a holographic wideband transceiver for operating said antenna units and providing each unit with millimeter wave radiation source, then receiving high frequency millimeter wave radiation reflection from said target and collected by the unit, then making an output;

(c) an analog to digital converter for converting said output to a corresponding digital signal; and (d) a computer for applying a three-dimensional reconstruction algorithm to the corresponding digital signal that preserves an unlimited depth of field.

2. The apparatus as recited in claim 1, wherein said antenna elements have a beam width from about 10 degrees to about 180 degrees.

3. The apparatus as recited in claim 1, wherein said antenna units are monostatic.

4. The apparatus as recited in claim 1, wherein said antenna units are bistatic.

5. The apparatus as recited in claim 2, wherein the antenna units are polyrod antennas.

6. The apparatus as recited in claim 2, wherein the antenna units are printed circuit antennas.

7. The apparatus as recited in claim 1, wherein the holographic array is interconnected to an electronic millimeter wave switch having a first set of pin diode switches in a first and second binary switch array.

8. The apparatus as recited in claim 1, wherein a beam width of the antenna element in combination with a distance from the transceiver to the target provides a low f-number.

9. The apparatus as recited in claim 1, wherein said output is an in-phase output.

10. The apparatus as recited in claim 1, wherein the computer for applying the image reconstruction algorithm comprises:

(a) a digital computer having, (i) a first set of instructions for receiving data from the A/D converter, (ii) a second set of instructions for computing a two-dimensional Fourier transform of the received data for each frequency, (iii) a third set of instructions for multiplying the two-dimensional Fourier transform by a complex backward wave propagator and forming a backward wave product, (iv) a fourth set of instructions for interpolating the backward wave product onto a uniformly sampled grid and forming an interpolated product, (v) a fifth set of instructions for computing a three-dimensional inverse transform of the interpolated product and obtaining a complex three-dimensional image, (vi) a sixth set of instructions for computing a magnitude of the complex three-dimensional image and obtaining a three-dimensional image, and (vii) a seventh set of instructions for displaying the three-dimensional image.

11. The apparatus as recited in claim 10, wherein the first set of instructions further comprises:

a subset of instructions for deriving complex data (Q) from in-phase data (I).

12. The apparatus as recited in claim 1, said array comprises:

a linear array, moved by a mechanical means during transmission and receipt of said high frequency millimeter wave radiation, thereby providing a simultaneous scan of source and reflection millimeter wave radiation.

13. The apparatus as recited in claim 12, wherein the linear array comprises:

(a) an upper horizontal row, and (b) a lower horizontal row wherein the two rows are offset by half the spacing between antenna elements, thereby enhancing horizontal resolution as the upper and lower horizontal rows are moved vertically.

14. The apparatus as recited in claim 12, wherein the two arrays are moved across an aperture in less than two seconds.

15. The apparatus as recited in claim 1, wherein a plurality of antenna elements are spaced in a stationary, multi-dimensional array.

16. The apparatus as recited in claim 15, wherein a multi-dimensional array is a planar two-dimensional array that is electronically scanned in less than 0.5 seconds.

17. The apparatus as recited in claim 1, wherein said antenna units are connected by a plurality of electronic millimeter wave switches permitting sequential operation of said antenna units.

18. The apparatus as recited in claim 1, wherein said transceiver is a bistatic, heterodyne, in-phase output transceiver.

19. The apparatus as recited in claim 18, wherein said bistatic, heterodyne, in-phase output transceiver is also non-tracking.

20. A method of holographic surveillance of a target, comprising the steps of:

(a) scanning a two-dimensional aperture with a holographic array having a plurality of antenna units spaced apart from about 0.25 to about 3 wavelength, wherein each unit sends and/or receives millimeter wave radiation, said array spaced apart from said target;

(b) operating individual antenna elements with a wideband holographic transceiver system and providing each unit with a wideband millimeter wave radiation source, then receiving wideband millimeter wave radiation reflection from said target and collected by the unit(s), then making an output;

(c) converting said output in an A/D converter to a corresponding digital signal; and (d) applying a three dimensional reconstruction algorithm to the digital signal that preserves a low f-number.

21. The method as recited in claim 20, wherein applying the three dimensional reconstruction algorithm includes applying a transform to derive an imaginary digital signal to reconstruct a holographic image.

22. The method as recited in claim 20, wherein said scanning is by sequential operating of said antenna units.

23. The method as recited in claim 20, wherein the applying the image reconstruction algorithm comprises the steps of:

(i) receiving data from the A/D converter, (ii) computing a two-dimensional Fourier transform of the received data for each frequency, (iii) multiplying the two-dimensional Fourier transform by a complex backward wave propagator and forming a backward wave product, (iv) interpolating the backward wave product onto a uniformly sampled grid and forming an interpolated product, (v) computing a three-dimensional inverse transform of the interpolated product and obtaining a complex three-dimensional image, (vi) computing a magnitude of the complex three-dimensional image and obtaining a three-dimensional image, and (vii) displaying the three-dimensional image.

24. The method as recited in claim 23, wherein receiving the data further comprises:

deriving complex data (Q) from in-phase data (I).

* * * * *

UNITED STATES PATENT AND TRADEMARK OFFICE
CERTIFICATE OF CORRECTION

PATENT NO. : 5,557,283
DATED : September 17, 1996
INVENTOR(S) : Sheen et al

It is certified that error appears in the above-indentified patent and that said Letters Patent is hereby corrected as shown below:

On the title page: before item [*] Notice:

insert item [73] Assignee to read -- Battelle Memorial Institute Richland, WA --.

In column 17, line 33, please replace the number "7" with --27--.

Item [57], under "Primary Examiner - Ian J. Lobo" add --Attorney, Agent or Firm - Paul W. Zimmerman--.

Signed and Sealed this

Eleventh Day of November, 1997

Attest:

BRUCE LEHMAN

Attesting Officer

Commissioner of Patents and Trademarks